US012697233B2

(12) United States Patent
Lenzi et al.

(10) Patent No.: US 12,697,233 B2
(45) Date of Patent: Aug. 4, 2026

(54) POWERED KNEE AND ANKLE PROSTHESIS CONTROLLER FOR ADAPTIVE AMBULATION

(71) Applicant: University of Utah Research Foundation, Salt Lake City, UT (US)

(72) Inventors: Tommaso Lenzi, Salt Lake City, UT (US); Lukas R. Gabert, Salt Lake City, UT (US); Liam Sullivan, Salt Lake City, UT (US); Marissa Ann Cowan, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 18/898,315

(22) Filed: Sep. 26, 2024

(65) Prior Publication Data

US 2025/0107907 A1 Apr. 3, 2025

Related U.S. Application Data

(60) Provisional application No. 63/541,700, filed on Sep. 29, 2023.

(51) Int. Cl.
*A61F 2/70* (2006.01)
*A61F 2/64* (2006.01)
(Continued)

(52) U.S. Cl.
CPC ................. *A61F 2/70* (2013.01); *A61F 2/64* (2013.01); *A61F 2/6607* (2013.01); *A61F 2/76* (2013.01);
(Continued)

(58) Field of Classification Search
CPC ...... A61F 2/64; A61F 2/68; A61F 2/70; A61F 2002/6607; A61F 2002/763; A61F 2002/7645
See application file for complete search history.

(56) References Cited

U.S. PATENT DOCUMENTS

| | | | |
|---|---|---|---|
| 8,623,098 | B2 | 1/2014 | Goldfarb et al. |
| 8,652,218 | B2 | 2/2014 | Goldfarb et al. |

(Continued)

FOREIGN PATENT DOCUMENTS

| | | |
|---|---|---|
| CA | 2762265 A1 | 10/2001 |
| CN | 114795604 A | 7/2022 |

(Continued)

OTHER PUBLICATIONS

Translation of WO2011057792A1 (Year: 2011).*

(Continued)

*Primary Examiner* — Christie Bahena
(74) *Attorney, Agent, or Firm* — Workman Nydegger

(57) ABSTRACT

Disclosed are embodiments of a volitional controller and prosthetic leg system comprising a volitional controller and a powered prosthetic leg. The volitional controller may be configured to control a powered knee joint and a powered ankle joint to enable a user to walk at different speeds and inclines. The orientation of the components of the powered prosthetic leg may be monitored continuously to enable the system to adapt to changes in the duration of the user's gait. The volitional controller may be configured to determine a target knee torque and a target ankle torque that may be based on the global shank orientation, a prosthetic knee velocity, and a prosthetic ankle velocity.

15 Claims, 8 Drawing Sheets

(51) Int. Cl.
   *A61F 2/66*        (2006.01)
   *A61F 2/76*        (2006.01)
(52) U.S. Cl.
   CPC . *A61F 2002/6614* (2013.01); *A61F 2002/763*
      (2013.01); *A61F 2002/7645* (2013.01)

(56)            References Cited

U.S. PATENT DOCUMENTS

| | | | |
|---|---|---|---|
| 8,696,764 | B2 | 4/2014 | Hansen et al. |
| 8,852,292 | B2 | 10/2014 | Ragnarsdottir et al. |
| 9,192,487 | B2 | 11/2015 | Flaven et al. |
| 9,221,177 | B2 | 12/2015 | Herr et al. |
| 9,248,031 | B2 | 2/2016 | Pusch et al. |
| 9,443,203 | B2 | 9/2016 | Young et al. |
| 9,649,207 | B2 | 5/2017 | Hahn et al. |
| 9,687,377 | B2 | 6/2017 | Han et al. |
| 9,763,809 | B2 | 9/2017 | Palmer et al. |
| 9,975,249 | B2 | 5/2018 | Herr et al. |
| 10,369,023 | B2 | 8/2019 | Simon et al. |
| 10,575,971 | B2 | 3/2020 | Herr et al. |
| 2002/0052663 | A1 | 5/2002 | Herr et al. |
| 2004/0167641 | A1 | 8/2004 | Kawai et al. |
| 2009/0265018 | A1 | 10/2009 | Goldfarb et al. |
| 2010/0241242 | A1 | 9/2010 | Herr et al. |
| 2012/0004736 | A1 | 1/2012 | Goldfarb et al. |
| 2012/0221120 | A1 | 8/2012 | Seyr et al. |
| 2012/0226364 | A1 | 9/2012 | Kampas et al. |
| 2013/0310949 | A1* | 11/2013 | Goldfarb .................. A61F 2/60 623/27 |
| 2014/0364962 | A1 | 12/2014 | Gregg et al. |
| 2015/0066156 | A1 | 3/2015 | Geyer et al. |
| 2015/0127119 | A1* | 5/2015 | Simon ...................... A61F 2/72 623/25 |
| 2015/0182354 | A1 | 7/2015 | Bonnet et al. |
| 2016/0058582 | A1* | 3/2016 | Lenzi ........................ A61F 2/70 623/24 |
| 2016/0302686 | A1 | 10/2016 | Sigurþórsson et al. |
| 2016/0338857 | A1 | 11/2016 | Herr et al. |
| 2017/0354529 | A1 | 12/2017 | Han et al. |
| 2023/0270570 | A1 | 8/2023 | Hofmann et al. |
| 2025/0107905 | A1 | 4/2025 | Lenzi et al. |
| 2025/0107908 | A1 | 4/2025 | Lenzi et al. |
| 2026/0090900 | A1 | 4/2026 | Lenzi et al. |
| 2026/0115019 | A1 | 4/2026 | Lenzi et al. |

FOREIGN PATENT DOCUMENTS

| | | | | |
|---|---|---|---|---|
| EP | 2849687 | B1 * | 7/2018 | ............... A61F 2/60 |
| WO | WO-2013067407 | A1 * | 5/2013 | ........... A61F 2/4657 |
| WO | 2016/130745 | A1 | 8/2016 | |
| WO | 2022/087160 | A1 | 4/2022 | |
| WO | 2022/087161 | A1 | 4/2022 | |

OTHER PUBLICATIONS

Alcock L., et al., "Biomechanical demands of the 2-step transitional gait cycles linking level gait and stair descent gait in older women," Journal of biomechanics, vol. 48, Issue 16, 2015, pp. 4191-4197.

Au S. et al., "Powered ankle-foot prosthesis to assist level-ground and stair-descent gaits," Neural Networks, vol. 21, Issue 4, 2008, pp. 654-666.

Best T. K. et al., "Data-Driven Variable Impedance Control of a Powered Knee-Ankle Prosthesis for Adaptive Speed and Incline Walking", IEEE Transactions on Robotics, 2023, pp. 19.

Ha K. H. et al., "Myoelectric control of a powered knee prosthesis for volitional movement during non-weight-bearing activities", 32nd Annual International Conference of the IEEE Embs., 2010, pp. 3515-3518.

Hood S. et al., "Powered Knee and Ankle Prosthesis with Adaptive Control Enables Climbing Stairs with Different Stair Heights, Cadences, and Gait Patterns", IEEE Trans Robot, vol. 38, Issue 3, Jun. 2022, pp. 1430-1441.

Huang H. et al., "A strategy for identifying locomotion modes using surface electromyography," IEEE Trans Biomed Eng, vol. 56, Issue 1, Jan. 2009, pp. 65-73.

Neuman R. M., et al., "There are unique kinematics during loco-motor transitions between level ground and stair ambulation that persist with increasing stair grade," Scientific Reports, vol. 13, Issue 1, 2023, 8576, pp. 11.

Non-Final Office Action received for U.S. Appl. No. 18/898,320, mailed on Nov. 20, 2024, 20 pages.

Peng J., et al., "Anticipatory kinematics and muscle activity pre-ceding transitions from level-ground walking to stair ascent and descent," Journal of biomechanics vol. 49, Issue 4, 2016, pp. 528-536.

Shultz, A. H. et al., "Variable cadence walking and ground adaptive standing with a powered ankle prosthesis," IEEE Trans Neural Syst Rehabil Eng., vol. 24, Issue 4, Apr. 2016, pp. 495-505.

Examiner Interview Summary Record Action received for U.S. Appl. No. 18/898,320, mailed on Mar. 13, 2025, 1 page.

Non-Final Office Action received for U.S. Appl. No. 18/898,303, mailed on Dec. 19, 2024, 8 pages.

\* cited by examiner

200

230    240    250    260

225    235    245    255

210    220

400

Determine a global shank
orientation
410

Determine a target ankle
torque based on the global
shank orientation
420

Determine a virtual biarticular
torque
430

Determine a target knee
torque based on the virtual
biarticular torque
440

Output a knee torque signal
for controlling a powered
knee joint of a powered leg
prosthesis
450

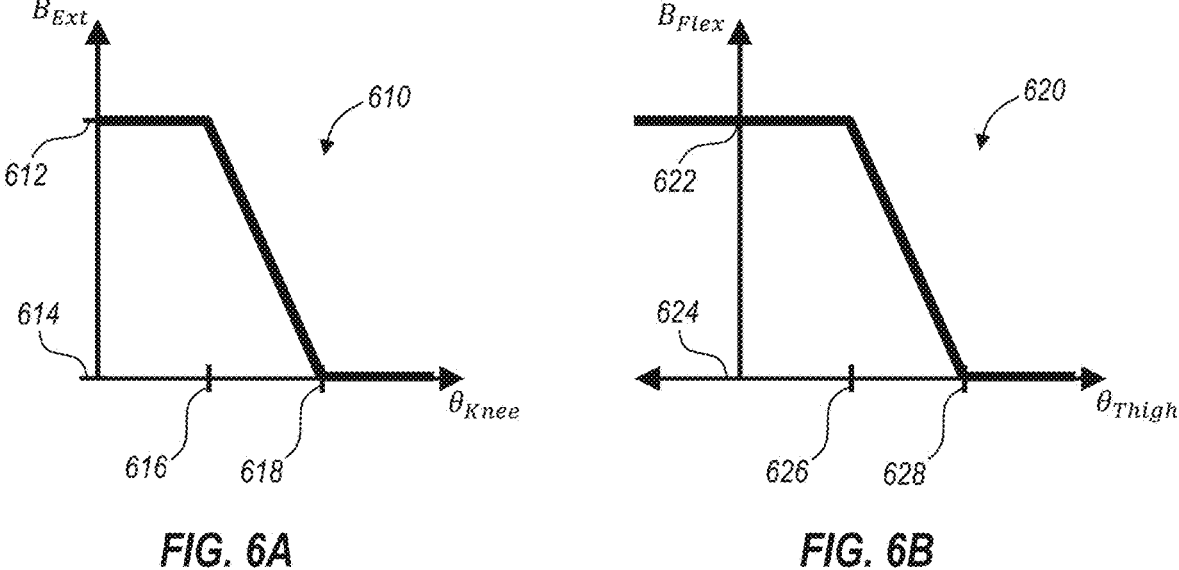
FIG. 6A
FIG. 6B
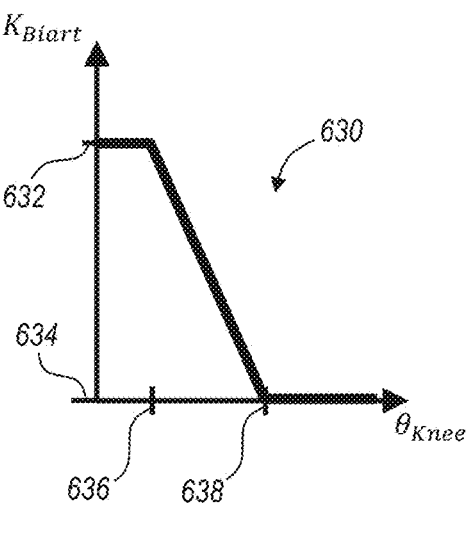
FIG. 6C

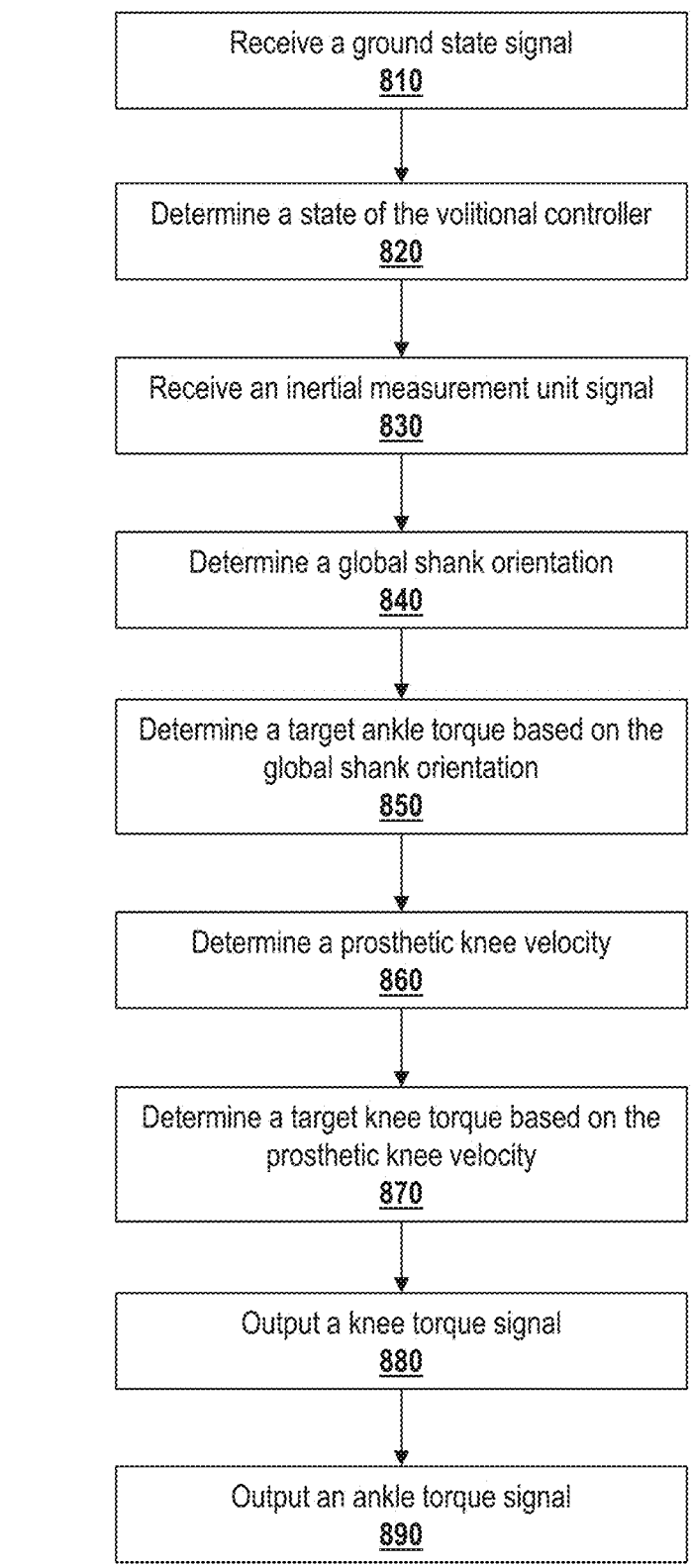

800

Receive a ground state signal
810

Determine a state of the volitional controller
820

Receive an inertial measurement unit signal
830

Determine a global shank orientation
840

Determine a target ankle torque based on the global shank orientation
850

Determine a prosthetic knee velocity
860

Determine a target knee torque based on the prosthetic knee velocity
870

Output a knee torque signal
880

Output an ankle torque signal
890

*FIG. 8*

POWERED KNEE AND ANKLE PROSTHESIS CONTROLLER FOR ADAPTIVE AMBULATION

CROSS-REFERENCE TO RELATED APPLICATIONS

This application claims priority to and the benefit of U.S. Provisional Patent Application Ser. No. 63/541,700, filed Sep. 29, 2023 and titled "Powered Knee and Ankle Prosthesis Controller for Adaptive Ambulation," the entirety of which is incorporated herein by reference.

STATEMENT REGARDING FEDERALLY SPONSORED RESEARCH

This invention was made with government support under W81XWH-21-1-0037 awarded by the Defense Health Agency, Medical Research and Development Branch, and R01 HD098154 awarded by the National Institutes of Health. The government has certain rights in the invention.

BACKGROUND

Technical Field

This disclosure relates to powered prosthetic limbs and controllers for operating powered prosthetic limbs.

Related Technology

Ambulation with conventional passive prostheses is slow and inefficient, resulting in poor mobility and quality of life for individuals with lower-limb amputations. Powered prostheses have the potential to address this problem by matching the torque, speed, and power capabilities of biological legs. However, the clinical viability of powered prostheses is limited by the ability of available controllers to adapt to the variability of the real world.

Some powered prosthesis controllers can adapt to discrete changes in speed and incline but require manual tuning to determine the control parameters, leading to poor clinical viability. Other data-driven controllers can continuously adapt to changes in speed and incline but do so by imposing the same non-amputee gait patterns for all amputee subjects, which does not consider subjective preferences and differing clinical needs of users.

Controllers that rely on manual tuning of the impedance settings during each discrete gait phase adapt to changes in speed and incline by defining behavior between discrete thresholds (e.g., negative 10 degree incline, 0 degree incline, 10 degree incline, or a slow, normal, or fast speed). This approach works well, but only close to the thresholds. Increasing the number of thresholds can improve function but is not clinically viable due to the time needed to manually determine the control parameters between each threshold and during each gait phase.

Accordingly, there is an ongoing need for prosthetic control systems capable of adapting to the variability of the real world during use.

SUMMARY

Disclosed are embodiments of volitional controllers, volitional controller and prosthetic leg systems, and methods executable by the volitional controllers for operating a powered leg prosthesis. The volitional controller may comprise one or more processors and one or more hardware storage devices having instructions stored thereon that are executable by the one or more processors to cause the controller to output a knee torque signal for controlling a powered knee joint of a powered leg prosthesis. The instructions may also cause the volitional controller to determine a global shank orientation, determine a target ankle torque based on the global shank orientation, determine a biarticular torque, and determine a target knee torque based on the biarticular torque before outputting the knee torque signal. These instructions may be executed without enforcing a specific prosthesis position, impedance, or torque by the controller. The instructions may further cause the controller to output an ankle torque signal for controlling the powered ankle joint of the powered leg prosthesis.

Determining the target knee torque may be further based on a first virtual damping torque. The first virtual damping torque can be proportional to and opposite a prosthesis knee velocity. The first virtual damping torque may be proportional to a knee gain coefficient, wherein the knee gain coefficient may be mapped to extension when a prosthetic knee velocity is negative and may be mapped to flexion when the prosthetic knee velocity is positive. The biarticular torque may be proportional to and opposite the target ankle torque and may increase with increasing ankle plantarflexion torque.

The target ankle torque can be based on a shank torque and which may be proportional to and opposite the global shank orientation. Determining the target ankle torque may be further based on a second virtual damping torque. The second virtual damping torque may be proportional to and opposite a prosthetic ankle velocity. In addition to being proportional to the prosthetic ankle velocity, the second virtual damping torque may be proportional to an ankle damping gain and wherein when a prosthetic ankle velocity is less than 0 degrees per second the ankle damping gain is mapped to dorsiflexion and when the prosthetic ankle velocity is greater than 0 degrees per second the ankle damping gain is mapped to plantarflexion.

The volitional controller may be configured to be arranged in a stance state and a swing state. The target knee torque may be output when the volitional controller is in the stance state and a target swing torque may be output when the volitional controller is in the swing state. When the volitional controller is in swing state, the instructions may further cause the volitional controller to determine a transition ankle orientation and determine a target swing torque based on the transition ankle orientation. Additionally, or alternatively, when the volitional controller is in swing state a desired end position of the knee and/or ankle joints may be determined using a minimum-jerk optimizer. The volitional controller may be configured to adapt to an incline and/or uneven terrain based solely on the global shank orientation.

The volitional controller may be connected with a powered leg prosthesis to form a powered leg prosthesis system. The powered leg prosthesis may comprise a shank having a proximal and a distal end. A powered knee joint may be connected to the proximal end of the shank and a powered ankle joint may be connected to the distal end of the shank. A prosthetic foot may be connected to the powered ankle joint. The powered leg prosthesis may comprise one or more sensors, including a GRF sensor and/or one or more IMU sensors for sending a ground state signal and/or determining the orientation of one or more components of the powered leg prosthesis.

The disclosure may comprise a method for controlling a powered leg prosthesis, the method comprising determining a global shank orientation, determining a target ankle torque based on the global shank orientation, determining a biarticular torque, determining a target knee torque based on the biarticular torque, and outputting a knee torque signal for controlling a powered knee joint of a powered leg prosthesis. The method may further comprise outputting an ankle torque signal for controlling a powered ankle joint of the powered leg prosthesis.

Also disclosed is a volitional controller configured to operate a powered knee and ankle prosthesis, the controller comprising one or more processors and one or more hardware storage devices having instructions that are executable by the one or more processors. The instructions may cause the volitional controller to at least receive a ground state signal, determine a state of the volitional controller, wherein the states of the volitional controller include stance state and swing state, receive an inertial measurement unit (IMU) signal, and determine a global shank orientation. The instructions may also cause the volitional controller to determine a target ankle torque based on the global shank orientation, determine a prosthetic knee velocity, determine a target knee torque based on the prosthetic knee velocity, output a knee torque signal for controlling a powered knee joint of a powered leg prosthesis, and output an ankle torque signal for controlling a powered ankle joint of the powered leg prosthesis.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

FIGS. 6A-6C illustrate the variability of gain values used to calculate the first virtual damping torque and the biarticular torque.

FIG. 8 illustrates another embodiment of a method comprising instructions that may be executed by the volitional controller.

DETAILED DESCRIPTION

Introduction

Figure 1:
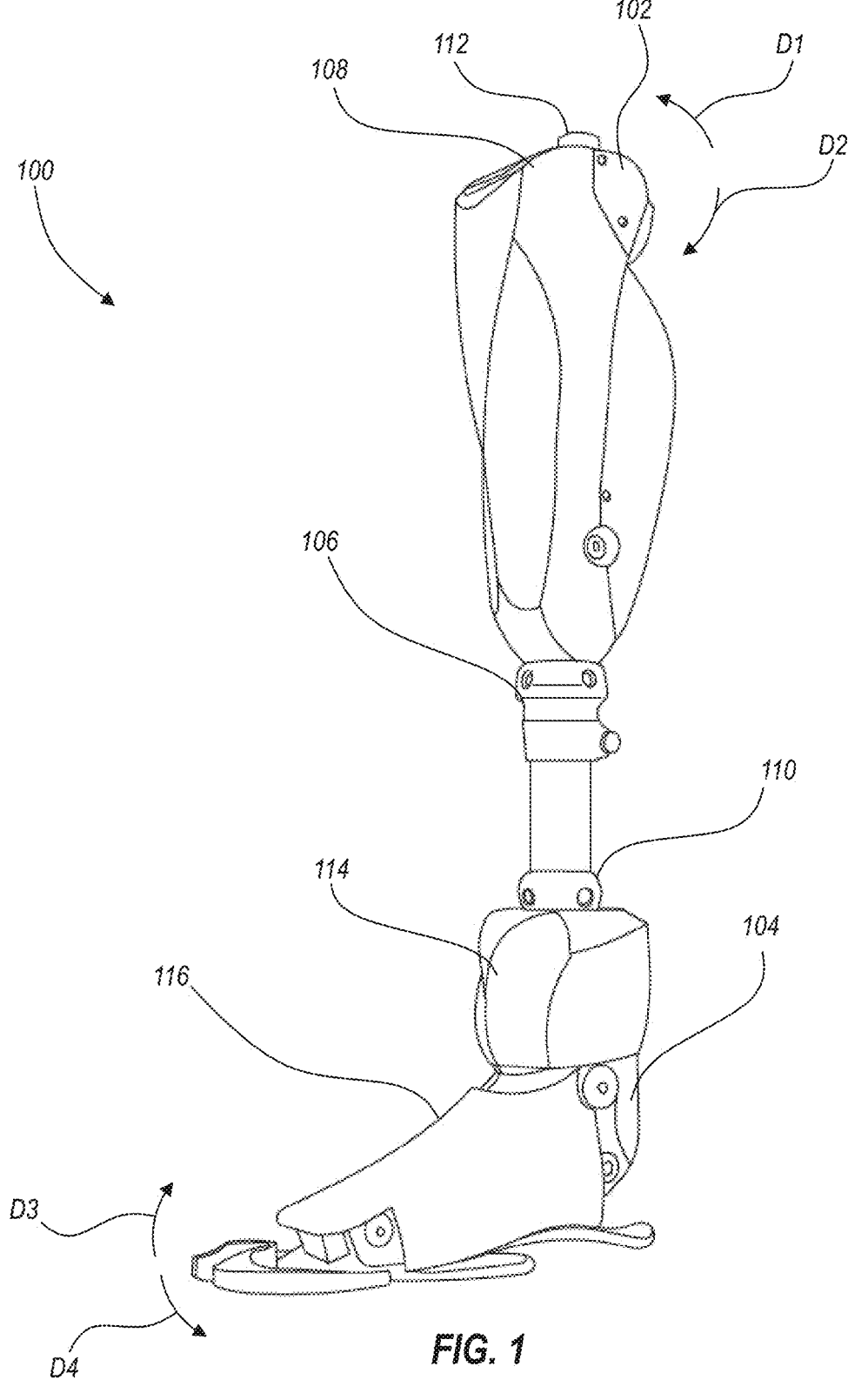
FIG. 1 illustrates an exemplary powered prosthetic leg.

Powered prosthesis controllers aim to imitate the biomechanical function of the human leg during ambulation. To this end, most controllers assume that the ambulation task is periodic and break down the gait cycle into a discrete number of phases or a continuous phase evolution, often using finite-state machines. Based on the online estimate of the discrete or continuous gait phase, the controller defines a desired torque, impedance, or position of the powered prosthesis joint. The specific values of the torque, impedance, and position for each gait phase can be manually tuned by the experimenter or automatically selected based on non-amputee datasets.

Many controllers attempt to predict duration of the gait phase and replicate ambulation movements based on periodic motion, but do not enable the prosthetic to adapt to deviations from a standard or preset gait phase. Some powered controllers provide repeat movements based on pre-recorded movement of non-amputated individuals, but such recordings may only be available at limited speed or may provide multiple speeds that represent various playback speeds of the recording. Detrimentally, these repeat movements do not adapt to variation within the gait phase or may provide variable gait speeds but at rigid un-adaptable speeds which may be uncomfortable to the user.

Machine learning models may be used to adapt the gait phase of the prosthesis to the gait of the user. However, these models may only adapt to the user after each step and may not adapt to the user mid-step. Thus, such models may not be adaptable to sudden changes in the duration of the gait or to changes in the terrain.

Disclosed herein are volitional prosthesis controllers that can continuously adapt to changes in gait speed or incline (i.e., continuous adaptation). The volitional controller may control a powered prosthesis to produce movements that resemble able-bodied kinematics and kinetics, particularly when compared with powered prosthetics exhibiting only discrete adaptation.

The volitional controller may not require manual tuning to adjust the powered prosthesis to the user. The controller can define the swing trajectory without assuming the movement is periodic and may enable ambulation at different speeds, at different inclines, on rough terrain, using a powered knee and ankle prosthesis.

This is achieved by continuously monitoring the characteristics of the prosthesis. Because the torque provided by the powered components of the powered prosthetic leg is determined by the ground state of the prosthesis and the orientation of the different components of the prosthesis, more specific positioning of the prosthetic foot and shank can be determined. This may enable the prosthesis to adapt to the terrain and gait speed according to the desire of the user. In this way, the volitional controller and prosthetic leg system may accurately provide the necessary torque to the powered components of the system without enforcing a specific position, impedance, or torque by the prosthesis.

Definitions

As used herein, the term "volitional controller" may refer to a device or group of devices configured to coordinate the performance of an electric motor. The volitional controller may be configured to provide control of a user to a prosthetic limb. The volitional controller may comprise one or more processors and/or one or more hardware storage devices. The volitional controller may comprise a computer or other device configured to algorithmically process incoming signals to operate a powered motor.

As used herein, the term "prosthetic limb" may refer to an artificial limb that replaces a missing body part. The prosthetic limb may primarily refer to a prosthetic leg configured to be attached to the upper leg of a trans-femoral amputee.

As used herein, the term "powered prosthesis," "powered prosthetic leg," or related terms may refer to a prosthetic limb that includes one or more electrical or powered components, such as electrical motors or sensors. The terms may also refer to a prosthetic limb comprising a powered or motored joint.

As used herein, the term "residual limb" may refer to the remaining part of a limb after an amputation. It may refer to the upper leg of a trans-femoral amputee.

As used herein, the term "wearable" or "wearable device" may refer to a device which is configured to be carried on the prosthesis and/or the body of the user.

As used herein, the term "gait cycle" may refer to the repetitive pattern of movement that occurs when a person walks or climbs a set of stairs.

As used herein, the term "ground surface" may refer to a surface with which the prosthetic foot of the powered prosthetic leg interacts during the gait cycle.

As used herein, the term "ground reaction force" (GRF) may refer to a force exerted on the prosthetic limb by the ground surface. The GRF sensor may measure a ground reaction force as the user places their weight on the prosthetic limb.

As used herein, the term "electromyography" (EMG) may refer to measurement of the electrical activity in the muscles and/or nerves that control the muscles.

As used herein, the term "inertial measurement unit" (IMU) may refer to a device that measures a body's specific force, angular rate, and/or orientation of the body. The IMU may incorporate accelerometers, gyroscopes, and/or magnetometers.

Powered Prosthetic Leg Components and Signals

FIG. 1 illustrates a powered prosthetic leg 100 that may comprise one or more powered components configured to be operated with the volitional controller described herein. The powered prosthetic leg 100 may comprise a distally-extending shank 106 having a proximal end 108 and a distal end 110, the shank 106 being configured to support the weight of a user. The shank 106 may be configured to receive one or more electrical components, including motors, wiring, sensors, or other components used to actuate the powered prosthetic leg 100. The shank 106 may widen near the proximal end 108 so as to house the one or more electrical components.

The powered prosthetic leg 100 may comprise a powered knee prosthesis. Specifically, the powered prosthetic leg 100 may comprise a powered knee joint 102 which may be configured to rotate the shank 106 along at least one axis in directions D1 and D2. The powered knee joint 102 may be located at or near the proximal end 108 of the shank 106 and may be located at a position that would correspond to the user's knee before amputation. The powered knee joint 102 may be configured to provide various levels of torque to enable the shank 106 of the powered prosthetic leg 100 to rotate relative to the residual limb and provide support to the user. The powered knee joint 102 may provide sufficient torque to lift the user and may provide a torque of approximately 10 Nm, approximately 20 Nm, approximately 30 Nm, approximately 40 Nm, approximately 50 Nm, approximately 60 Nm, approximately 70 Nm, or more than approximately 70 Nm, or may provide a torque within a range having any two of the foregoing as endpoints The distal end 110 of the shank 106 may be connected to a prosthetic foot 116 via a powered ankle joint 104. The powered ankle joint 104 may be configured to rotate the prosthetic foot 116 relative to the shank 106 along at least one axis in directions D3 and D4. The prosthetic foot 116 may comprise one or more additional powered components configured to facilitate the walking and climbing movement of the user. The powered ankle joint 104 may be similarly configured as the powered knee joint 102 described above and may be capable of providing a torque to rotate the prosthetic foot 116 and lift the user during the gait cycle 200. The powered ankle joint 104 may be configured to provide the same amounts of torque, including the amounts and ranges of torque, as the powered knee joint 102 described above. In some embodiments, the powered ankle joint 104 may be smaller than the powered knee joint 102 and may be configured to provide less torque than the powered knee joint 102.

The powered ankle joint 104 may be connected to the distal end 110 of the shank 106 by a distal adapter 114 (e.g., a pyramid adapter) configured to facilitate connection between the prosthetic foot 116 and the shank 106. The distal adapter 114 may be detachable from the shank 106 to allow different configurations of a prosthetic foot 116 and powered ankle joint 104 to be attached to the powered prosthetic leg 100. The shank 106 and distal adapter 114 may comprise an interior or lumen extending along its length configured to house wiring that may power the powered knee joint 102 and powered ankle joint 104. Additionally, or alternatively, the wiring may extend along an exterior of the shank 106 and/or distal adapter 114.

The powered prosthetic leg 100 may be configured to receive the residual limb of a user. Specifically, the powered prosthetic leg 100 may comprise a prosthetic socket configured to receive the residual limb. The socket may be configured to receive the residual limb of a trans-femoral amputee (wherein the leg has been amputated above the knee), such that the socket is configured to receive the residual limb of the upper leg of a user. The prosthetic socket may be formed about the residual limb of the user. For example, the socket may be formed through a molding process such that the socket forms a comfortable and tight fit with the user's residual limb. The socket may be attached to a proximal adapter 112 extending from the powered knee joint 102.

In this manner, the powered knee joint 102 may be configured to, at least in part, replace the knee joint of the amputee user. The powered knee joint 102 may rotate the shank 106 relative to the upper leg of the user to enable the powered prosthetic leg 100 to flex and extend. This flexion and extension may enable the powered prosthetic leg 100 to provide a more natural ambulatory motion during walking by the user, particularly when adjusting gait speed, gait length, foot placement, ground surface incline, or other adjustment. The powered ankle joint 104 may rotate the prosthetic foot 116 to mimic the dorsiflexion (wherein the prosthetic foot 116 rotates in direction D3) and plantarflexion (wherein the prosthetic foot 116 rotates in direction D4) of a non-amputee. The dorsiflexion and plantarflexion may enable the prosthetic foot 116 to more accurately flex similar to a non-amputee foot to provide a more natural movement of the powered prosthetic leg 100. The powered prosthetic leg 100 may comprise metals, such as aluminum, steel, stainless steel, or titanium, or may comprise polymers, such as carbon fiber, glass fiber, or other lightweight and rigid plastics, or may comprise a composite material.

The volitional controller may be connected to one or more sensors attached to or disposed about the powered prosthetic leg 100 that may be used to activate the powered knee joint 102 or the powered ankle joint 104 and which may be used to receive signals for determining a target torque to be exerted by the powered knee joint 102 and/or the powered ankle joint 104. In this manner, the one or more sensors may be wearable, such that the one or more sensors are carried by the user on the powered prosthetic leg 100.

The one or more sensors may be configured to determine when the powered prosthetic leg system is in contact with a ground surface. For example, the volitional controller may be connected to a ground a ground reaction force (GRF) sensor that may measure the amount of force placed on the powered prosthetic leg 100 to support the user. In a broad sense, the GRF sensor may be used to determine if the powered prosthetic leg 100 is in contact with the ground. The GRF sensor may be disposed on or connected to the powered prosthetic leg 100. The GRF sensor may be disposed within the distal adapter 114 connecting the powered ankle joint 104 to the shank 106. In other embodiments, the GRF sensor may be disposed within or attached to the prosthetic foot 116 or to the shank 106. In some embodiments, the GRF sensor may be attached to the proximal adapter 112 or may be attached to or disposed within the socket. The GRF sensor may comprise a wearable force plate that measures the force between the powered prosthetic leg 100 and a ground surface and may indicate when the powered prosthetic leg 100 is in contact with or off the ground surface.

The one or more sensors may be configured to determine the orientation of the residual limb of the user, the orientation of the shank 106, and/or the orientation of the prosthetic foot 116. The powered prosthetic leg system may comprise one or more inertial measurement unit (IMU) sensors. The IMU sensor(s) may be configured to measure motion and/or orientation of the residual limb and the powered prosthetic leg 100. The IMU sensor(s) may be attached to various parts of the powered prosthetic leg 100, the socket, and/or the user. For example, the system may comprise a first IMU sensor attached to the socket or the residual limb of the user. One or more IMU sensors may be attached to the powered prosthetic leg 100, such as at the shank 106 or the prosthetic foot 116. In this way, the IMU signals from one or more IMU sensors may provide the relative orientation between the residual limb and the powered prosthetic leg 100. In other embodiments, the system may comprise only one IMU sensor. The one IMU sensor may be disposed at the proximal end 108 of the powered prosthetic leg 100. Because the position of the proximal end 108 of the powered prosthetic leg 100 is determined by movement of the residual limb and because the one IMU sensor will rotate relative to the powered knee joint 102 along with the shank 106 of the powered prosthetic leg 100, the one IMU sensor may provide the orientation of the residual limb as well as the orientation of the shank 106. Similarly, an IMU sensor may be attached to the prosthetic foot 116 at or near the proximal end of the foot 116 near the powered ankle joint 104 and in line with the shank 106. In this manner, the IMU sensor may measure the rotation of the prosthetic foot 116 as well as the movement of the distal end 110 of the shank 106.

The one or more sensors may also be configured to measure the activation of one or more muscles of the user. In such instances, the activation of the powered prosthetic leg 100 may be dependent on the activation the one or more muscles of the user. For example, the one or more sensors may comprise an electromyography (EMG) sensor comprising an electrode configured to measure the activation of an EMG signal source, such as a muscle in the residual limb. The EMG signal may be amplified before it is received by the volitional controller. The powered prosthetic leg 100 may activate only when the EMG signal source activates. In this manner, control of the powered prosthetic leg 100 may be more intuitive to the user, such that the user may replicate movements similar to pre-amputee walking movements to activate the powered prosthetic leg 100.

The volitional controller may be attached to a portion of the powered prosthetic leg system, such as to a portion of the powered prosthetic leg 100. For example, the volitional controller may be attached to or disposed within the shank 106. The volitional controller may be attached to the one or more sensors, including the GRF sensor, IMU sensor(s), and/or EMG sensor. The volitional controller may be connected to the one or more sensors by wiring that extends from the sensors to the controller. The wiring may extend along an exterior of the socket and/or the powered prosthetic leg 100, but preferably extends within the socket and the powered prosthetic leg 100 so as to prevent environmental obstacles from snagging the wiring.

The volitional controller may comprise a computer or other hardware device configured to receive one or more inputs and to provide an output of a target torque to the powered knee joint 102 and/or the powered ankle joint 104. The volitional controller may comprise one or more processors and may be connected to one or more hardware storage devices that include instructions for operating the volitional controller. In some embodiments, the volitional controller may comprise a computer system.

The volitional controller may comprise one or more hardware storage devices. The one or more hardware storage devices may be configured to store signal data measured by the one or more sensors. The one or more hardware storage devices may be configured to store instructions to be implemented by the volitional controller. The one or more hardware storage devices may comprise a computer readable storage medium that includes volatile and non-volatile, removable and non-removable media, implemented with any technology for the storage of information such as computer readable instructions, data structures, program modules, or other data. Computer readable storage media includes, but is not limited to, a non-transitory machine readable storage medium, such as RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology.

Gait Cycle

Figure 2:
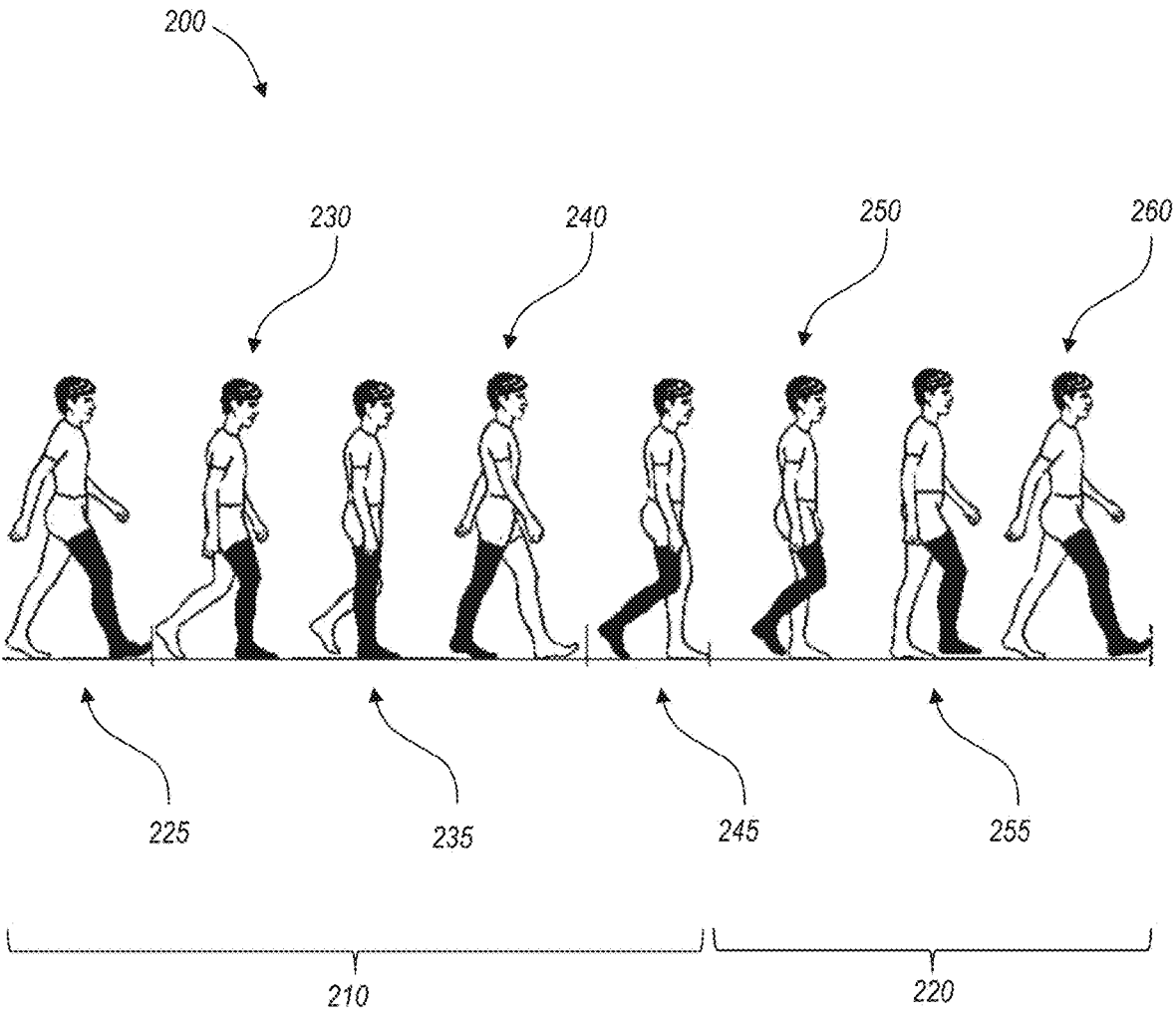
FIG. 2 illustrates a conventional gait cycle.

FIG. 2 illustrates a diagram of a user during the gait cycle 200, a discussion of which may be useful in understanding the features of the volitional controller and prosthetic leg system described herein. The gait cycle 200 is described with respect to one limb—the limb of interest—and typically comprises two phases: stance phase 210 and swing phase 220. In stance phase 210, the limb of interest is in contact with the ground surface and bears the weight of the body. Stance phase 210 begins with heel strike 225 and progresses therefrom through loading response 230, mid-stance 235, terminal stance 240, and finally to pre-swing 245. At the end of pre-swing 245, the limb of interest transitions from stance phase 210 to swing phase 220 in which the limb of interest is raised from the ground. Swing phase 220 then progresses from the end of pre-swing 245 through toe-off 250, mid-swing 255, and terminal swing 260. After terminal swing 260, the limb of interest is brought back in contact with the ground surface at heel strike 225 to start stance phase 210 and begin another gait cycle 200.

During stance phase 210, the limb of interest is extended, with the knee and ankle joints extending, to push the upper body forwards. Thus, during stance phase 210, the limb of interest moves from an anterior position to a posterior position relative to the upper body. At pre-swing 245, as weight is taken off of the limb of interest, the knee joint is flexed to enable the limb of interest to rise above the ground surface as the limb of interest is brought from a posterior position to an anterior position. The knee joint of the limb of interest may then undergo partial extension before the limb of interest is brought back in contact with the ground surface at heel strike 225.

Orientation of the Powered Prosthetic Leg

Figure 3:
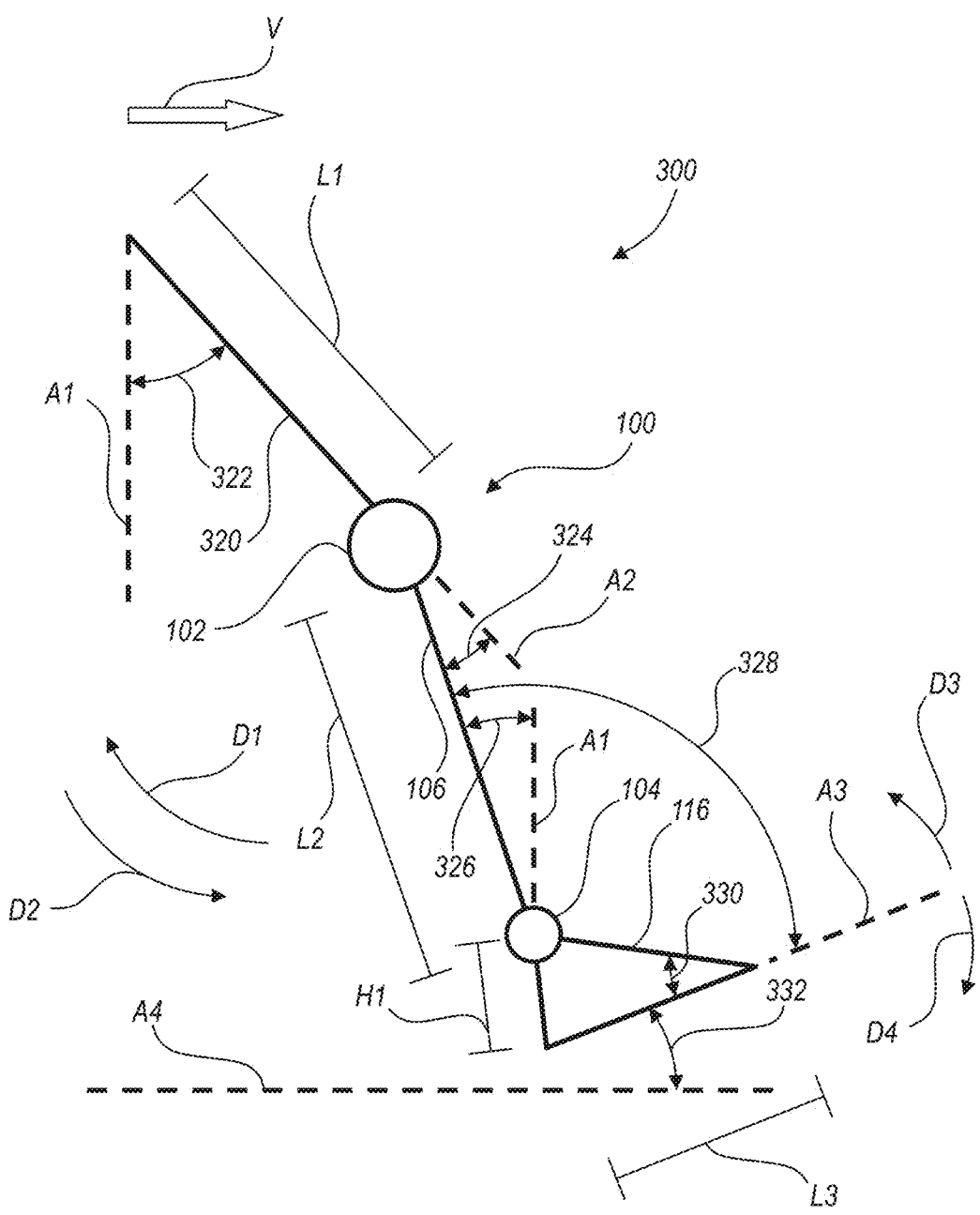
FIG. 3 illustrates a schematic of the powered prosthetic leg.

FIG. 3 illustrates a diagram 300 of the powered prosthetic leg 100 organized in as a simple schematic. The diagram 300 illustrates the components of the powered prosthetic leg 100, including a powered knee joint 102 and a powered ankle joint 104 connected to a shank 106 as well as a prosthetic foot 116 connected to the powered ankle joint 104. Also illustrated is the residual limb 320 (including the upper leg and prosthetic socket) that is connected to the powered knee joint 102. One or more characteristics of the components of the powered prosthetic leg 100 may be stored on the one or more hardware storage devices, such as the length L1 (i.e., $l_{Thigh}$) of the residual limb, the length L2 (i.e., $l_{Shank}$) of the shank 106, the height H1 at which the prosthetic foot 116 extends from the ground surface, and the length L3 (i.e., $l_{Foot}$) at which the prosthetic foot 116 extends along the ground surface. Another characteristic may include the hip velocity V defined as the speed of motion of the hip (e.g., along a horizontal line) that may be used to estimate the walking speed of the user. These and other characteristics may be used by the volitional controller to determine the positions and orientation of the components of the powered prosthetic leg 100.

Also illustrated are various axes that will be helpful in understanding the relative orientation of the components of the powered prosthetic leg 100. The axes include a first axis A1 which is oriented in a generally vertical direction, a second axis A2, a third axis A3, and a fourth axis A4. The first axis A1 may extend in the general direction of gravity or may extend in the direction of the normal force acting through the user's non-amputated leg or another prosthetic leg of the user. The second axis A2 may extend inline with or pass through the center of the residual limb of the user. The third axis A3 extends in line with the lower surface ## of the prosthetic foot 116 and the fourth axis A4 may extend in a direction that is generally perpendicular to the first axis A1, such that the fourth axis A4 may be generally horizontal, extending generally perpendicular to the direction of gravity or the normal force passing through the users other leg.

By receiving signals from the one or more sensors, such as one or more IMU sensors, the volitional controller may determine one or more orientations related to the powered prosthetic leg 100. The volitional controller may determine a global thigh orientation 322 (i.e., $\theta_{Thigh}$) defined as the angle between the residual limb and the first axis A1 or as the angle between the first axis A1 and the second axis A2. The global thigh orientation 322 may be positive when the residual limb is positioned posterior of the torso of the user and may be negative when the residual limb is positioned anterior of the torso of the user. The volitional controller may similarly determine a global shank orientation 326 (i.e., $\theta_{Shank}$) defined as the angle between the shank 106 (or a line passing through the center of the shank 106) and the first axis A1. The global shank orientation 326 may similarly be positive when the shank 106 is located posterior of the torso of the user and may be negative when the shank 106 is located anterior of the torso. The volitional controller may determine a knee angle 324 (i.e., $\theta_{Knee}$) defined as the angle between the shank 106 (or a line passing through the center of the shank 106) and the second axis A2.

The volitional controller may determine other orientations, including an ankle orientation 328 (i.e., $\theta_{Ankle}$), a foot orientation 332 (i.e., $\theta_{Foot}$), and a toe angle 330 (i.e., a). The ankle orientation 328 may be defined as the angle between the shank 106 (or a line passing through the center of the shank 106) and the third axis A3 extending along the lower surface of the prosthetic foot 116. The foot orientation 332 may be defined as the angle between the third axis A3 extending along the lower surface of the prosthetic foot 116 and the fourth axis A4. The toe angle 330 may be defined as the angle between the upper and lower surfaces of the prosthetic foot 116.

Figure 4:
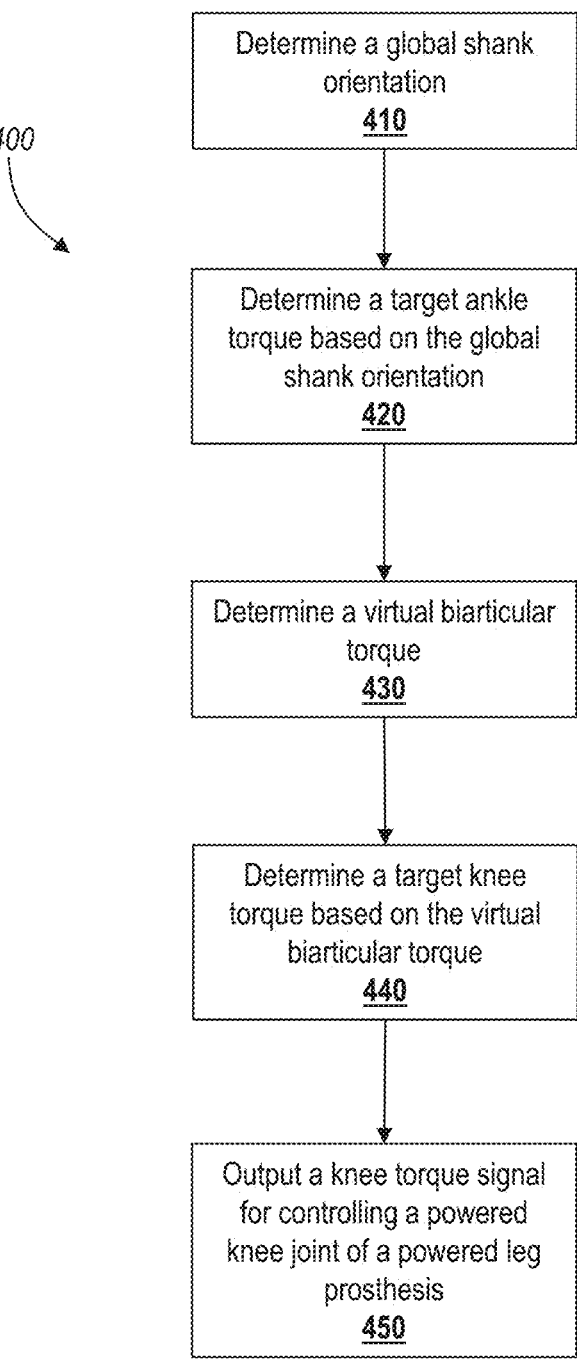
FIG. 4 illustrates a method comprising instructions that may be executed by the volitional controller.

FIG. 4 illustrates a method 400 comprising instructions that may be implemented by the volitional controller. The instructions may cause the volitional controller to determine a global shank orientation 410. Based on the global shank orientation the volitional controller may determine a target ankle torque 420 (i.e., $T_{Ankle}$). Thereafter, the volitional controller may determine a biarticular torque 430 (i.e., $T_{Biart}$). The biarticular torque may depend on the target ankle torque that was previously determined. The volitional controller may then be caused to determine a target knee torque (i.e., $T_{Knee}$) based on the biarticular torque 440. The volitional controller may then output a knee torque signal for controlling a powered knee joint 102 of a powered leg prosthesis 450. The volitional controller may further output an ankle torque signal for controlling a powered ankle joint 104 of a powered prosthetic leg 100. The above method 400 may be performed after the volitional controller receives one or more signal from the one or more sensors.

The volitional controller may be arranged to be configured in a swing state and a stance state. The output of the volitional controller and/or the instructions performed may depend on the state of the volitional controller. For example, all of the instructions of the method 400 may be performed while the volitional controller is in stance state, but may omit any or all of the instructions when the volitional controller is in swing state.

The state of the volitional controller may be determined by a finite-state machine. The logic and/or processing of the finite-state machine may be formed as part of the volitional controller or may be formed as part of another circuit or controller configured to alter the state of the volitional controller. The finite-state machine may be configured to receive a GRF signal from a GRF sensor to determine whether the powered prosthetic leg 100 is in contact with the ground (and therefore in stance phase 210). The finite-state machine may be configured to configure the volitional controller in stance state when the GRF signal rises above an upper GRF threshold and to configure the volitional controller in swing state when the GRF signal falls below a lower GRF threshold.

The upper GRF threshold may be greater than the lower GRF threshold. The upper GRF threshold may be set to a value within a range from approximately 40 N to approximately 160 N, or from approximately 50 N to approximately 155 N, or from approximately 60 N to approximately 150 N, or from approximately 70 N to approximately 145 N, or from approximately 80 N to approximately 140 N, or from approximately 90 N to approximately 135 N, or from approximately 100 N to approximately 130 N, or from approximately 110 N to approximately 135 N, or from approximately 115 N to approximately 120, or within a range having any two of the foregoing as endpoints. Similarly, the lower GRF threshold may be set to a value within a range from approximately 20 N to approximately 80 N, or from approximately 25 N to approximately 70 N, or from approximately 30 N to approximately 60 N, or from approximately 35 N to approximately 50 N, or may be set to approximately 40 N, or may be set within a range having any two of the foregoing as endpoints. The upper and lower GRF thresholds may be determined by the weight and/or age of the user. For example, the one or both of the GRF thresholds may be greater for a person weighing more than 200 pounds than for a person weighing between 120 and 150 pounds.

For example, the upper GRF threshold may be set at 120 N and the lower GRF threshold may be set at 40 N. At heel strike 225, when a user places a load on the powered prosthetic leg 100, the GRF may then provide a GRF signal above 120 N such that the finite-state machine configures the volitional controller in stance state. The volitional controller may then remain in stance state until the GRF signal falls below the lower GRF threshold. That is, the volitional controller then remains in stance state while the GRF signal falls below the upper GRF threshold until the GRF signal falls below the lower GRF threshold. At pre-swing 245, the user may remove the load from the powered prosthetic leg 100 such that the GRF signal falls below the lower GRF threshold and the finite state machine configures the volitional controller in swing state until the load on the powered prosthetic leg 100 again rises above the upper GRF threshold.

Target Knee Torque

Figure 5:
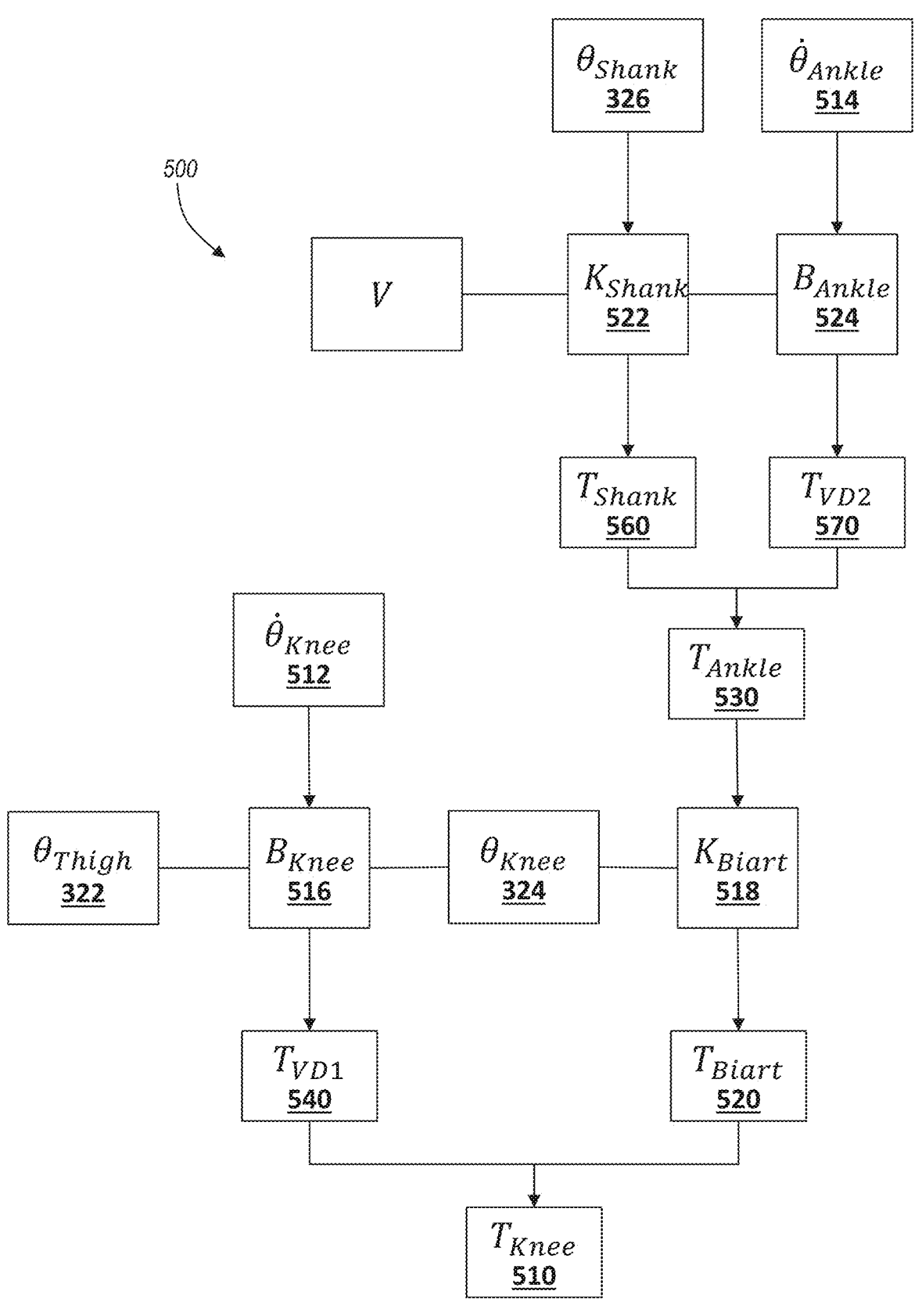
FIG. 5 illustrates a schematic of the determination of the target knee torque and the target ankle torque by the volitional controller.

FIG. 5 illustrates a schematic 500 of the process by which a target knee torque 510 and a target ankle torque 530 are determined. Importantly, the process illustrated by FIG. 5 used to determine the target knee torque 510 and the target ankle torque 530 may be used only when the volitional controller is in the stance state. Alternatively, the process of schematic 500 may be employed in either stance or swing state.

The target knee torque 510 can be determined as the sum of a biarticular torque and first virtual damping torque 540 (i.e., $T_{VD1}$), as in the following relationship: $T_{Knee}=T_{VD1}+T_{Biart}$. The first virtual damping torque 540 is dependent on the prosthetic knee velocity 512 (i.e., $\dot{\theta}_{Knee}$), with the prosthetic knee velocity 512 representing the change in knee angle 324. Specifically, the first virtual damping torque 540 can be proportional to and opposite the prosthetic knee velocity 512, such as illustrated in the following relationship: $T_{VD1}=-B_{Knee}\cdot\dot{\theta}_{Knee}$. The first virtual damping torque 540 is thus determined by the product of the prosthetic knee velocity 512 and the negative of a knee gain coefficient 516 ($B_{Knee}$), such that the first virtual damping torque 540 is proportional to the knee gain coefficient 516.

The knee gain coefficient 516 is a gain that may be dependent on the prosthetic knee velocity and either the knee angle 324 or the global thigh orientation 322. If the prosthetic knee velocity 512 is negative (i.e., if the powered knee joint is in extension) then the knee gain coefficient 516 is mapped to an extension gain. If the prosthetic knee velocity 512 is positive (i.e., if the powered knee joint in in flexion) then the knee gain coefficient 516 is mapped to a flexion gain.

FIGS. 6A-6B illustrate the values of the extension and flexion gains. FIG. 6A illustrates a relationship 610 showing that the extension gain may be dependent on the knee angle 324. The extension gain may have a maximum value 612 and a minimum value 614. For example, the maximum value

612 of the extension gain may be approximately 0.1 and the minimum value 614 of the extension gain may be approximately 0, such that the extension gain exhibits a value between approximately 0 and approximately 0.1. The extension gain may be at a maximum value 612 when the knee angle 324 is at or below the lower threshold 616 and may be at a minimum value 614 when the knee angle 324 is at or above the upper threshold 618.

The lower and upper thresholds 616, 618 may each be configured at one of various values. The lower threshold 616 may be set within a range from approximately 5 degrees to approximately 20 degrees, or from approximately 6 degrees to approximately 18 degrees, or from approximately 7 degrees to approximately 15 degrees, or from approximately 8 degrees to approximately 12 degrees, or may be set to approximately 10 degrees, or may be set within a range having any two of the foregoing as endpoints. The upper threshold 618 may be set within a range from approximately 10 degrees to approximately 40 degrees, or from approximately 12 degrees to approximately 35 degrees, or from approximately 15 degrees to approximately 30 degrees, or from approximately 18 degrees to approximately 25 degrees, or may be set to approximately 20 degrees, or may be set within a range having any two of the foregoing as endpoints. However, the values of the maximum value 612, minimum value 614, lower threshold 616, and the upper threshold 618 may differ than described above depending on the particular characteristics and/or dimensions of the powered prosthetic leg 100 for which the controller is configured to operate.

The extension gain may be linearly related to the knee angle 324 between the lower and upper thresholds 616, 618. Alternatively, the extension gain may be linearly related to the knee angle 324 over only a portion of the range between the lower and upper thresholds 616, 618 or may have another relationship with the knee angle 324, such as an exponential or logarithmic relationship, or a binomial, trinomial, or other polynomial relationship.

FIG. 6B illustrates a relationship 620 showing that the flexion gain may depend on the global thigh orientation 322. The flexion gain may have a maximum value 622 and a minimum value 624. For example, the maximum value 622 may of the flexion gain may be approximately 0.3 and the minimum value 624 of the flexion gain may be approximately 0, such that the flexion gain exhibits a value between approximately 0 and approximately 0.3. The flexion gain may similar to the extension gain may be at a maximum value 622 when the global thigh orientation is at or below a lower threshold 626 and may be at a minimum value 624 when the global thigh orientation is at or above an upper threshold 628.

The lower and upper thresholds 626, 628 may each be configured at one of various values. The lower threshold 626 may be set within a range from approximately 1 degree to approximately 10 degrees, or from approximately 2 degrees to approximately 8 degrees, or from approximately 3 degrees to approximately 7 degrees, or from approximately 4 degrees to approximately 6 degrees, or may be set to approximately 5 degrees, or may be set within a range having any two of the foregoing as endpoints. The upper threshold 628 may be set within a range from approximately 5 degrees to approximately 20 degrees, or from approximately 6 degrees to approximately 18 degrees, or from approximately 7 degrees to approximately 16 degrees, or from approximately 8 degrees to approximately 14 degrees, or from approximately 9 degrees to approximately 12 degrees, or may be set to approximately 10 degrees, or may be set within a range having any two of the foregoing as endpoints. However, similar to the values 612, 614 and thresholds 616, 618 described above, the values of the maximum value 622, minimum value 624, lower threshold 626, and the upper threshold 628 may differ than described above depending the particular characteristics and/or dimensions of the powered prosthetic leg 100 for which the controller is configured to operate. The maximum value 622 of the flexion gain may be greater than the maximum value 612 of the extension gain.

Similar to the extension gain, the flexion gain may be linearly related to the global thigh orientation 322 between the lower and upper thresholds 626, 628. Alternatively, the flexion gain may be linearly related to the global thigh orientation 322 over only a portion of the range between the lower and upper thresholds 626, 628 or may have another relationship with the global thigh orientation 322, such as an exponential or logarithmic relationship, or a binomial, trinomial, or other polynomial relationship.

Thus, in at least one embodiment, the first virtual damping torque may be determined as the prosthetic knee velocity 512 multiplied by the negative of an extension gain between the value of 0 and 0.1 (when the powered knee joint 102 is in extension) or multiplied by the negative of a flexion gain between the value of 0 and 0.3 (when the powered knee joint 102 is in flexion).

The biarticular torque 520 is configured so as to imitate the function of the gastrocnemius muscle, which extends the foot downwards in plantarflexion to propel a person forward and stabilizes the knee during ambulation. The biarticular torque 520 may be proportional to and opposite the target ankle torque 530. Specifically, the biarticular torque 520 may be configured to increase with ankle plantarflexion torque. The relationship between the biarticular torque and the target ankle torque 530 may be given as follows: $T_{Biart}=-K_{Biart} \cdot T_{Ankle}$, such that the biarticular torque 520 is determined by multiplying the target ankle torque 530 by the negative of a biarticular gain coefficient 518 ($K_{Biart}$).

FIG. 6C illustrates a relationship 630 showing that the biarticular gain coefficient 518 may depend on the knee angle 324. The biarticular gain coefficient 518 may have a maximum value 632 and a minimum value 634. For example, the maximum value 632 of the biarticular gain coefficient 518 may be approximately 0.5 and the minimum value 634 of the biarticular gain coefficient 518 may be approximately 0, such that the biarticular gain coefficient 518 exhibits a value between approximately 0 and approximately 0.1. The biarticular gain coefficient 518 may be at a maximum value 632 when the knee angle 324 is at or below the lower threshold 636 and may be at a minimum value when the knee angle 324 is at or above the upper threshold 638.

The lower and upper thresholds 636, 638 may each be configured at one of various values. The lower threshold 636 may be set within a range from approximately 10 degrees to approximately 30 degrees, or from approximately 12 degrees to approximately 28 degrees, or from approximately 15 degrees to approximately 25 degrees, or from approximately 18 degrees to approximately 22 degrees, or may be set to approximately 20 degrees, or may be set within a range having any two of the foregoing as endpoints. The upper threshold 638 may be set within a range from approximately 20 degrees to approximately 45 degrees, or from approximately 22 degrees to approximately 40 degrees, or from approximately 25 degrees to approximately 35 degrees, or from approximately 27 degrees to approximately 33 degrees, or may be set to approximately 30 degrees, or may be set within a range having any two of the foregoing as endpoints. However, the values of the maximum value 632, minimum value 634, lower threshold 636, and the upper threshold 638 may differ than described above depending on the particular characteristics and/or dimensions of the powered prosthetic leg 100 for which the controller is configured to operate.

The biarticular gain coefficient 518 may be linearly related to the knee angle 324 between the lower and upper thresholds 616, 618. Alternatively, the biarticular gain coefficient 518 may be linearly related to the knee angle 324 over only a portion of the range between the lower and upper thresholds 616, 618 or may have another relationship with the knee angle 324, such as an exponential or logarithmic relationship, or a binomial, trinomial, or other polynomial relationship.

Target Ankle Torque

The target ankle torque 530 may be determined as the sum of two torque components, including a shank torque 560 ($T_{Shank}$) and a second virtual damping torque 570 (i.e., $T_{VD2}$), and may be illustrated by the following relationship: $T_{Ankle}=T_{Shank}+T_{VD2}$. The shank torque 560 may be proportional to and opposite the global shank orientation 326, as illustrated in the following relationship: $T_{Shank}=-K_{Shank} \cdot \theta_{Shank}$. Specifically, the shank torque 560 may be determined as the product of the global shank orientation 326 and the negative of a shank gain coefficient 522 (i.e., $K_{Shank}$). As the incline increases, the shank 106 may be positioned relatively anterior (such that the global shank orientation 326 is negative) for a larger portion of the gait cycle 200. Because the shank torque 560 increases with greater negative angles of the global shank orientation 326, the shank torque 560 increases as the incline increases. In this way, the determination of the target ankle torque 530 may be based on the global shank orientation 326 and may adapt to changes in the incline or to uneven terrain based solely on the global shank orientation 326.

Figure 7A:
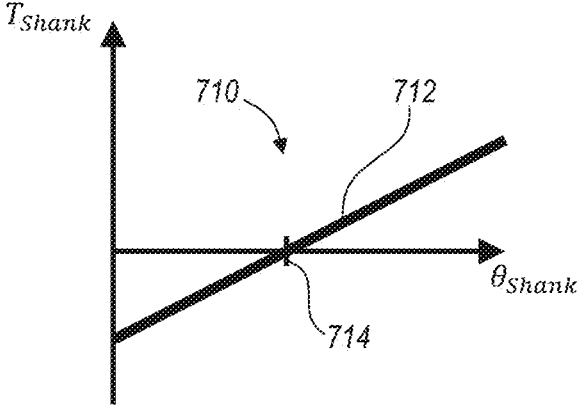
FIG. 7A illustrates the relationship between the global shank orientation and the shank torque.

FIG. 7A illustrates graph 710 that further shows the relationship between the global shank orientation 326 and the shank torque 560. Graph 710 also illustrates that the shank gain coefficient 522, representing the slope of the shank torque line 712, may be constant over a wide range of angles of the global shank orientation 326. The shank torque 560, as a component of the target ankle torque 530, may be equivalent to creating a virtual ankle stiffness. Specifically, the shank torque 560 may be proportional to the angular difference between the gravity vector (i.e., the direction of gravity) and the shank 106 or a line passing through the center of the shank 106 (illustrated as the shank torque line 712 reaches no torque at point 714 wherein the global shank orientation 326 is at 0 degrees). In this manner, the shank torque 560 works to push the shank 106 back to a vertical position regardless of the ankle position. This virtual stiffness increases proportional to the global shank orientation 326, which replicates or better mimics the ankle stiffness observed in non-amputee individuals.

The second virtual damping torque 570 may be proportional to and opposite a prosthetic ankle velocity 514 (i.e., θAnkle), with the prosthetic ankle velocity 514 representing the change in the ankle orientation 328. The second virtual damping torque 570 may be determined by the following relationship: $T_{VD2}=-B_{Ankle} \cdot \dot{\theta}_{Ankle}$. The second virtual damping torque 570 may thus be defined as the product of the prosthetic ankle velocity 514 and the negative of an ankle damping gain 524 (i.e., $B_{Ankle}$).

The ankle damping gain 524 may be mapped to a dorsiflexion gain or a plantarflexion gain depending on the value of the prosthetic ankle velocity 514. If the prosthetic ankle velocity 514 is negative (i.e., when the prosthetic ankle velocity is less than 0 degrees per second and the prosthetic foot 116 is in dorsiflexion or rotating in the direction D3) then the ankle damping gain 524 can be mapped to the dorsiflexion gain. If the prosthetic ankle velocity 514 is positive (i.e., when the prosthetic ankle velocity is more than 0 degrees per second and the prosthetic foot 116 is in plantarflexion or rotating in the direction D4) then the ankle damping gain 524 can be mapped to the plantarflexion gain. As a non-limiting example, the angle of the ankle orientation 328 may decrease during stance from loading response 230 through mid-stance 235, such that the prosthetic foot 116 is in dorsiflexion. Then, beginning in terminal stance 240 through pre-swing 245, the angle of the ankle orientation 328 may increase, such that the prosthetic foot 116 is in plantarflexion.

Figure 7B:
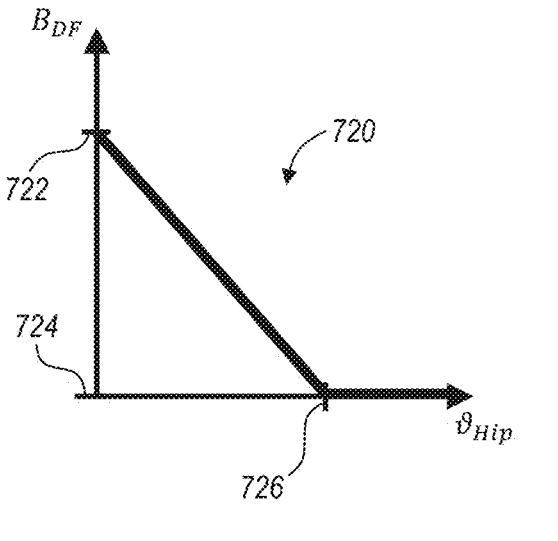
FIGS. 7B-7C illustrate the variability of gain values used to calculate the second virtual damping torque.
Figure 7C:
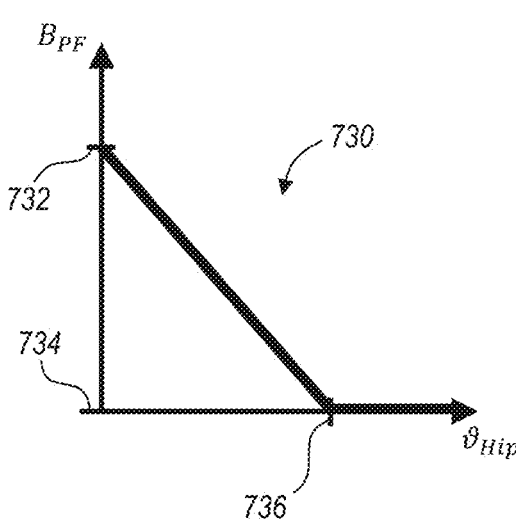

FIGS. 7B-7C illustrate that the dorsiflexion and plantarflexion gains may depend on a hip velocity V, which is used to estimate the walking speed in stance phase 210. The hip velocity V may be determined by the following relationship: $\dot{\vartheta}_{Hip}=(\sin(\alpha+\theta_{Foot})\cdot l_{Foot}\cdot\dot{\theta}_{Foot})+(\cos(\theta_{Shank})\cdot l_{Shank}\cdot\dot{\theta}_{Shank})+(\cos(\theta_{Thigh})\cdot l_{Thigh}\cdot\dot{\theta}_{Thigh})$. Thus, the hip velocity may be determined as a function of the prosthetic foot velocity (i.e., $\dot{\theta}_{Foot}$, defined as the change in the foot orientation 332), the prosthetic shank velocity (i.e., $\dot{\theta}_{Shank}$, defined as the change in the global shank orientation 326), and the residual limb velocity (i.e., $\dot{\theta}_{Thigh}$, defined as the change in the global thigh orientation 322).

FIG. 7B illustrates the relationship 720 between the dorsiflexion gain and the hip velocity V. The dorsiflexion gain may have a maximum value 722 and a minimum value 724. For example, the maximum value 722 of the dorsiflexion gain may be approximately 1.3 and the minimum value 724 of the dorsiflexion gain may be approximately 0, such that the dorsiflexion gain exhibits a value between approximately 0 and approximately 1.3. The dorsiflexion gain may be at a maximum value 722 when the hip velocity V is at or near 0 m/s and may be at a minimum value when the hip velocity V is at or above a velocity threshold 726.

The velocity threshold 726 may be configured at one of various values. The velocity threshold 726 may be set within a range from approximately 1.0 m/s to approximately 1.5 m/s, or from approximately 1.1 m/s to approximately 1.45 m/s, or from approximately 1.2 m/s to approximately 1.4 m/s, or may be set to approximately 1.3 m/s, or may be set within a range having any two of the foregoing as endpoints. However, the values of the maximum value 722, minimum value 724, and the velocity threshold 726 may differ than described above depending on the particular characteristics and/or dimensions of the powered prosthetic leg 100 for which the controller is configured to operate.

The dorsiflexion gain may be linearly related to the hip velocity V between a value at or near 0 m/s and the velocity threshold 726. Alternatively, the dorsiflexion gain may be linearly related to the hip velocity V over only a portion of the range between a hip velocity V at or near 0 and the velocity threshold 726 or may have another relationship with the hip velocity V, such as an exponential or logarithmic relationship, or a binomial, trinomial, or other polynomial relationship.

FIG. 7C illustrates the relationship 730 between the plantarflexion gain and the hip velocity V. The plantarflexion gain may have a maximum value 732 and a minimum value 734. For example, the maximum value 732 of the plantarflexion gain may be approximately 1.2 and the minimum value 734 of the plantarflexion gain may be approximately 0, such that the plantarflexion gain exhibits a value between approximately 0 and approximately 1.2. The plantarflexion gain may be at a maximum value 732 when the hip velocity V is at or near 0 m/s and may be at a minimum value when the hip velocity V is at or above a velocity threshold 736.

The velocity threshold 736 may be configured at one of various values. The velocity threshold 736 may be set within a range from approximately 0.4 m/s to approximately 1.2 m/s, or from approximately 0.5 m/s to approximately 1.0 m/s, or from approximately 0.6 m/s to approximately 0.9 m/s, or from approximately 0.7 m/s to approximately 0.8 m/s, or may be set within a range having any two of the foregoing as endpoints. However, the values of the maximum value 732, minimum value 734, and the velocity threshold 736 may differ than described above depending on the particular characteristics and/or dimensions of the powered prosthetic leg 100 for which the controller is configured to operate.

The plantarflexion gain may be linearly related to the hip velocity V between a value at or near 0 m/s and the velocity threshold 736. Alternatively, the plantarflexion gain may be linearly related to the hip velocity V over only a portion of the range between a hip velocity V at or near 0 and the velocity threshold 736 or may have another relationship with the hip velocity V, such as an exponential or logarithmic relationship, or a binomial, trinomial, or other polynomial relationship.

FIG. 8 illustrates another method 800 similar to method 400 described above that includes instructions that may be executed by the volitional controller. Specifically, the instructions of method 800 may be executed when the controller is in the stance state. The method 800 is presented as another description of the instructions, as described above, that may be executed by the one or more processors of the volitional controller.

Within the method 800, the volitional controller may first receive a ground state signal 810 and then determine a state of the volitional controller 820 (e.g., based on the ground state signal), wherein the states of the volitional controller include stance state and swing state. The volitional controller may then receive an inertial measurement unit (IMU) signal 830 to determine a global shank orientation 840. Thereafter, the volitional controller may determine a target ankle torque based on the global shank orientation 850. Using information stored on the one or more hardware storage devices (e.g., the IMU signal), the volitional controller may then determine a prosthetic knee velocity 860. The volitional controller may then determine a target knee torque based on the prosthetic knee velocity 870. The volitional controller may then output a knee torque signal 880 and may output an ankle torque signal 890 for controlling the powered knee joint 102 and the powered ankle joint 104, respectively, of the powered prosthetic leg 100.

Swing Phase

When the received GRF signal rises above the upper GRF threshold, the finite-state machine may configure the volitional controller to the swing state. In contrast to the methods 400 and 800 that may be used to provide an adaptive powered prosthetic leg system, the torque and position of the powered prosthetic leg 100 may be determined based on a desired end position, for example, of the knee and/or ankle joints, the shank 106 and/or the prosthetic foot 116, or the powered prosthetic leg 100 as whole. The desired end position may include an end knee position or orientation and/or an end ankle position or orientation. Specifically, from a flexed position at the end of pre-swing

245, the powered knee joint 104 may be extended to an end knee position during swing phase 220 in preparation for heel strike 225.

A target swing torque (i.e., $T_{Swing}$) may be determined to achieve the desired knee angle 324 of the desired end position. The target swing torque may also be configured so as to provide a smooth trajectory of the shank 106 according to the duration of the swing phase 220 of the gait cycle 200. In particular, a minimum-jerk optimizer may be employed to determine the desired positions of the knee and ankle joints, such that there are minimal changes to the angular acceleration of the shank 106 and/or the prosthetic knee velocity 512, ensuring an even smooth rotation of the shank 106 from a posterior position to an anterior position during swing phase 220.

The target swing torque may depend on the ankle orientation at the transition from stance phase to swing phase. In a non-amputee individual, as walking speed increases so too does the cadence of the gait cycle, reducing the duration of swing phase 220. As walking speed increases the ankle orientation at the transition between stance and swing (i.e., transition ankle orientation or $\theta_{Transition}$) also increases. Therefore, to increase the prosthetic knee velocity, the target swing torque may be increased as the transition ankle orientation increases. The determination of the target swing orientation in swing state may be defined by the following relationship: $T_{Swing} = K_{Swing} \cdot \theta_{Transition}$, such that the target swing torque may be determined as the product of the transition ankle orientation and a swing gain coefficient (i.e., $K_{Swing}$). That is, the target swing torque may be proportional to transition ankle orientation. The target swing torque may then be output by the volitional controller for controlling the powered knee joint 104.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

The various features of a given embodiment can be combined with and/or incorporated into other embodiments disclosed herein. Thus, disclosure of certain features relative to a specific embodiment of the present disclosure should not be construed as limiting application or inclusion of said features to the specific embodiment. Rather, it will be appreciated that other embodiments can also include such features.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 10%, less than 5%, less than 1%, less than 0.1%, or less than 0.01% of the stated amount, value, or condition.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

The embodiments disclosed herein should be understood as comprising/including disclosed components, and may therefore include additional components not specifically described. Optionally, the embodiments disclosed herein are essentially free or completely free of components that are not specifically described. That is, non-disclosed components may optionally be completely omitted or essentially omitted from the disclosed embodiments.

Example Aspects

The following clauses provide a non-exhaustive list of example aspects of the disclosed volitional controller for a powered knee prosthesis:

Clause 1. A volitional controller for a powered lower leg prosthesis, comprising: one or more processors; and one or more hardware storage devices having instructions stored thereon that are executable by the one or more processors to cause the controller to at least: determine a global shank orientation; determine a target ankle torque based on the global shank orientation; determine a biarticular torque; determine a target knee torque based on the biarticular torque; and output a knee torque signal for controlling a powered knee joint of a powered leg prosthesis based on the determined target knee torque, wherein the controller does not enforce a specific prosthesis position, impedance, or torque.

Clause 2. The volitional controller of clause 1, wherein the instructions further cause the controller to output an ankle torque signal for controlling the powered ankle joint of the powered leg prosthesis.

Clause 3. The volitional controller of any preceding clause, wherein determining the target knee torque is further based on a first virtual damping torque, wherein the first virtual damping torque is proportional to and opposite a prosthesis knee velocity.

Clause 4. The volitional controller of clause 3, wherein the first virtual damping torque is proportional to a knee gain coefficient and wherein the knee gain coefficient is mapped to extension when a prosthetic knee velocity is negative and is mapped to flexion when the prosthetic knee velocity is positive.

Clause 5. The volitional controller of any preceding clause, wherein the biarticular torque is proportional to and opposite the target ankle torque.

Clause 6. The volitional controller of any preceding clause, wherein the biarticular torque increases with ankle plantarflexion torque.

Clause 7. The volitional controller of any preceding clause, wherein determining the target ankle torque is further based on a shank torque, wherein the shank torque is proportional to and opposite the global shank orientation.

Clause 8. The volitional controller of any preceding clause, wherein determining the target ankle torque is further based on a second virtual damping torque, wherein the second virtual damping torque is proportional to and opposite a prosthetic ankle velocity.

Clause 9. The volitional controller of clause 8, wherein the second virtual damping torque is proportional to an ankle damping gain and wherein when a prosthetic ankle velocity is less than 0 degrees per second the ankle damping gain is mapped to dorsiflexion and when the prosthetic ankle velocity is greater than 0 degrees per second the ankle damping gain is mapped to plantarflexion.

Clause 10. The volitional controller of any preceding clause, wherein the volitional controller is configured to adapt to an incline and/or uneven terrain based solely on the global shank orientation.

Clause 11. The volitional controller of any preceding clause, wherein the volitional controller is configured to be arranged in a stance state and a swing state; and wherein the target knee torque is output when the volitional controller is in the stance state.

Clause 12. The volitional controller of clause 11, wherein the instructions, when the volitional controller is in swing state, cause the volitional controller to: determine an ankle transition orientation; and determine a target swing torque based on the ankle transition orientation.

Clause 13. The volitional controller of clause 11 or clause 12, wherein when the volitional controller is in swing state a desired end position of the knee and/or ankle joints is determined using a minimum-jerk optimizer.

Clause 14. A powered leg prosthesis system configured to provide volitional control to a user, the system comprising: a powered leg prosthesis; and the controller of any preceding clause.

Clause 15. The powered leg prosthesis system of clause 14, wherein the powered leg prosthesis comprises: a shank having a proximal and a distal end; a powered knee joint connected to the proximal end of the shank; a powered ankle joint connected to the distal end of the shank; and a prosthetic foot connected to the powered ankle joint.

Clause 16. The powered leg prosthesis system of clause 14 or clause 15, wherein the powered leg prosthesis comprises a GRF sensor and/or one or more IMU sensors.

Clause 17. A method for controlling a powered leg prosthesis, optionally using a powered leg prosthesis as in any of clauses 14-16, comprising: determining a global shank orientation; determining a target ankle torque based on the global shank orientation; determining a biarticular torque; determining a target knee torque based on the biarticular torque; and outputting a knee torque signal for controlling a powered knee joint of a powered leg prosthesis.

Clause 18. The method of clause 17, further comprising outputting an ankle torque signal for controlling a powered ankle joint of the powered leg prosthesis.

Clause 19. The method of clause 17 or clause 18, wherein determining the target knee torque is further based on a first virtual damping torque, wherein the first virtual damping torque is proportional to and opposite a prosthesis knee velocity.

Clause 20. A volitional controller configured to operate a powered knee and ankle prosthesis, the controller comprising: one or more processors; one or more hardware storage devices having stored thereon instructions that are executable by the one or more processors to cause the volitional controller to at least: receive a ground state signal; determine whether the prosthesis is in stance phase or swing phase based on the ground state signal; determine a state of the volitional controller, wherein the states of the volitional controller include stance state and swing state; receive an inertial measurement unit (IMU) signal; determine a global shank orientation; determine a target ankle torque based on the global shank orientation; determine a prosthetic knee velocity; determine a target knee torque based on the prosthetic knee velocity; output a knee torque signal for controlling a powered knee joint of a powered leg prosthesis;

and output an ankle torque signal for controlling a powered ankle joint of the powered leg prosthesis.

The invention claimed is:

1. A powered leg prosthesis system, comprising:
a powered leg prosthesis comprising a shank that includes a proximal end and a distal end, a powered knee joint connected to the proximal end of the shank, a powered ankle joint connected to the distal end of the shank, and a prosthetic foot connected to the powered ankle joint; and
a volitional controller, the volitional controller comprising one or more processors and one or more hardware storage devices having instructions stored thereon that are executable by the one or more processors to cause the controller to at least:
determine a global shank orientation, wherein the global shank orientation is the angle between the shank of the powered lower leg prosthesis and direction of gravity;
determine a target ankle torque based on the global shank orientation;
determine a biarticular torque based on the target ankle torque;
determine a target knee torque based on the biarticular torque; and
output a knee torque signal for controlling the powered knee joint of the powered leg prosthesis based on the determined target knee torque,
wherein the biarticular torque is proportional to and opposite the target ankle torque.

2. The powered leg prosthesis system of claim 1, wherein the instructions further cause the controller to output an ankle torque signal for controlling the powered ankle joint of the powered leg prosthesis based on the determined target ankle torque.

3. The powered leg prosthesis system of claim 1, wherein determining the target knee torque is further based on a first virtual damping torque, wherein the first virtual damping torque is proportional to and opposite a prosthesis knee velocity.

4. The powered leg prosthesis system of claim 1, wherein the biarticular torque increases with ankle plantarflexion torque.

5. The powered leg prosthesis system of claim 1, wherein determining the target ankle torque is further based on a shank torque, wherein the shank torque is proportional to and opposite the global shank orientation.

6. The powered leg prosthesis system of claim 1, wherein determining the target ankle torque is further based on a second virtual damping torque, wherein the second virtual damping torque is proportional to and opposite a prosthetic ankle velocity.

7. The powered leg prosthesis system of claim 1, wherein the volitional controller is configured to adapt to an incline and/or uneven terrain based solely on the global shank orientation.

8. The powered leg prosthesis system of claim 1, wherein the target knee torque is output by the volitional controller when the volitional controller determines that the powered leg prosthesis is in a stance state.

9. The powered leg prosthesis system of claim 8, wherein the instructions, when the volitional controller determines that the powered leg prosthesis is in a swing state, cause the volitional controller to:
determine an ankle transition orientation; and
determine a target swing torque based on the ankle transition orientation.

10. The powered leg prosthesis system of claim 8, wherein when the volitional controller determines that the powered leg prosthesis is in a swing state, a desired end position of the knee and/or ankle joints is determined using a minimum-jerk optimizer.

11. The powered leg prosthesis system of claim 1, wherein the powered leg prosthesis comprises a ground reaction force sensor and/or one or more IMU sensors.

12. A powered leg prosthesis system, comprising:

a powered leg prosthesis comprising a shank that includes a proximal end and a distal end, a powered knee joint connected to the proximal end of the shank, a powered ankle joint connected to the distal end of the shank, and a prosthetic foot connected to the powered ankle joint; and a volitional controller, the volitional controller comprising one or more processors and one or more hardware storage devices having instructions stored thereon that are executable by the one or more processors to cause the controller to at least:

determine a global shank orientation, wherein the global shank orientation is the angle between the shank of the powered lower leg prosthesis and direction of gravity;

determine a target ankle torque based on the global shank orientation;

determine a biarticular torque based on the target ankle torque;

determine a target knee torque based on the biarticular torque; and output a knee torque signal for controlling the powered knee joint of the powered leg prosthesis based on the determined target knee torque, wherein the biarticular torque increases with ankle plantarflexion torque.

13. A powered leg prosthesis system, comprising:

a powered leg prosthesis comprising a shank that includes a proximal end and a distal end, a powered knee joint connected to the proximal end of the shank, a powered ankle joint connected to the distal end of the shank, and a prosthetic foot connected to the powered ankle joint; and a volitional controller, the volitional controller comprising one or more processors and one or more hardware storage devices having instructions stored thereon that are executable by the one or more processors to cause the controller to at least:

determine a global shank orientation, wherein the global shank orientation is the angle between the shank of the powered lower leg prosthesis and direction of gravity;

determine a target ankle torque based on the global shank orientation;

determine a biarticular torque based on the target ankle torque;

determine a target knee torque based on the biarticular torque; and output a knee torque signal for controlling the powered knee joint of the powered leg prosthesis based on the determined target knee torque, wherein determining the target ankle torque is further based on a shank torque, wherein the shank torque is proportional to and opposite the global shank orientation.

14. A powered leg prosthesis system, comprising:

a powered leg prosthesis comprising a shank that includes a proximal end and a distal end, a powered knee joint connected to the proximal end of the shank, a powered ankle joint connected to the distal end of the shank, and a prosthetic foot connected to the powered ankle joint; and a volitional controller, the volitional controller comprising one or more processors and one or more hardware storage devices having instructions stored thereon that are executable by the one or more processors to cause the controller to at least:

determine a global shank orientation, wherein the global shank orientation is the angle between the shank of the powered lower leg prosthesis and direction of gravity;

determine a target ankle torque based on the global shank orientation;

determine a biarticular torque based on the target ankle torque;

determine a target knee torque based on the biarticular torque; and output a knee torque signal for controlling the powered knee joint of the powered leg prosthesis based on the determined target knee torque, wherein determining the target ankle torque is further based on a second virtual damping torque, wherein the second virtual damping torque is proportional to and opposite a prosthetic ankle velocity.

15. A powered leg prosthesis system, comprising:

a powered leg prosthesis comprising a shank that includes a proximal end and a distal end, a powered knee joint connected to the proximal end of the shank, a powered ankle joint connected to the distal end of the shank, and a prosthetic foot connected to the powered ankle joint; and a volitional controller, the volitional controller comprising one or more processors and one or more hardware storage devices having instructions stored thereon that are executable by the one or more processors to cause the controller to at least:

determine a global shank orientation, wherein the global shank orientation is the angle between the shank of the powered lower leg prosthesis and direction of gravity;

determine a target ankle torque based on the global shank orientation;

determine a biarticular torque based on the target ankle torque;

determine a target knee torque based on the biarticular torque; and output a knee torque signal for controlling the powered knee joint of the powered leg prosthesis based on the determined target knee torque, wherein determining the target knee torque is further based on a first virtual damping torque, wherein the first virtual damping torque is proportional to and opposite a prosthesis knee velocity.

\* \* \* \* \*